United States Patent
Felty et al.

(10) Patent No.: US 7,913,985 B2
(45) Date of Patent: Mar. 29, 2011

(54) CAP

(75) Inventors: Dave Felty, Parma, OH (US); Christopher Delgado, Glendale, AZ (US); Sam Shelnutt, North Ridgeville, OH (US); Gregory Flolid, Barrington, IL (US)

(73) Assignee: Invacare Corporation, Elyria, OH (US)

( * ) Notice: Subject to any disclaimer, the term of this patent is extended or adjusted under 35 U.S.C. 154(b) by 1054 days.

(21) Appl. No.: 11/684,284

(22) Filed: Mar. 9, 2007

(65) Prior Publication Data

US 2007/0210462 A1  Sep. 13, 2007

Related U.S. Application Data

(60) Provisional application No. 60/780,789, filed on Mar. 9, 2006.

(51) Int. Cl.
*B01F 3/04* (2006.01)

(52) U.S. Cl. ............... 261/72.1; 261/119.1; 261/DIG. 65

(58) Field of Classification Search .................. 261/142, 261/72.1, 119.1, 121.1, DIG. 65
See application file for complete search history.

(56) References Cited

U.S. PATENT DOCUMENTS

| | | | |
|---|---|---|---|
| 3,441,161 A | 4/1969 | Van Baam | |
| 3,568,871 A | 3/1971 | Livingstone | |
| 4,098,853 A * | 7/1978 | Brown et al. | 261/122.1 |
| 4,464,316 A * | 8/1984 | Michaels | 261/121.1 |
| 4,566,603 A | 1/1986 | Moore | |
| 4,657,713 A * | 4/1987 | Miller | 261/142 |
| 4,819,625 A * | 4/1989 | Howe | 128/200.18 |
| 4,907,709 A | 3/1990 | Abe et al. | |
| 4,943,704 A * | 7/1990 | Rabenau et al. | 392/386 |
| 5,105,961 A | 4/1992 | Noren et al. | |
| 5,301,667 A * | 4/1994 | McGrail et al. | 128/205.14 |
| 5,383,558 A | 1/1995 | Wilkinson et al. | |
| 5,489,036 A | 2/1996 | Arkins | |
| 5,558,084 A * | 9/1996 | Daniell et al. | 128/203.17 |
| 5,931,323 A | 8/1999 | Wilkinson et al. | |
| 6,869,065 B1 * | 3/2005 | Lin | 261/3 |
| 6,918,389 B2 * | 7/2005 | Seakins et al. | 128/203.27 |
| 7,413,173 B2 * | 8/2008 | DiMatteo et al. | 261/142 |

OTHER PUBLICATIONS

Operator's Manual, Invacare Polaris EX Heated Humidifier, Model No. ISP4000, 11 pgs., Nov. 2003.
Operator's Manual, Invacare Polaris EX Heated Humidifier, Model No. ISP4000, 20 pgs., Oct. 2004.

* cited by examiner

*Primary Examiner* — Scott Bushey
(74) *Attorney, Agent, or Firm* — Calfee Halter & Griswold LLP

(57) ABSTRACT

A container cap for providing a seal with an annular wall of a receptacle is disclosed. The cap includes a top wall, an annular seal wall, and cam structure. The annular seal wall extends axially from the cover portion. The annular seal wall is spaced radially inward of the cam structure. An end portion of the annular seal wall is configured to form a seal with the annular wall of the receptacle when the end portion is forced into engagement with annular wall of the receptacle.

33 Claims, 9 Drawing Sheets

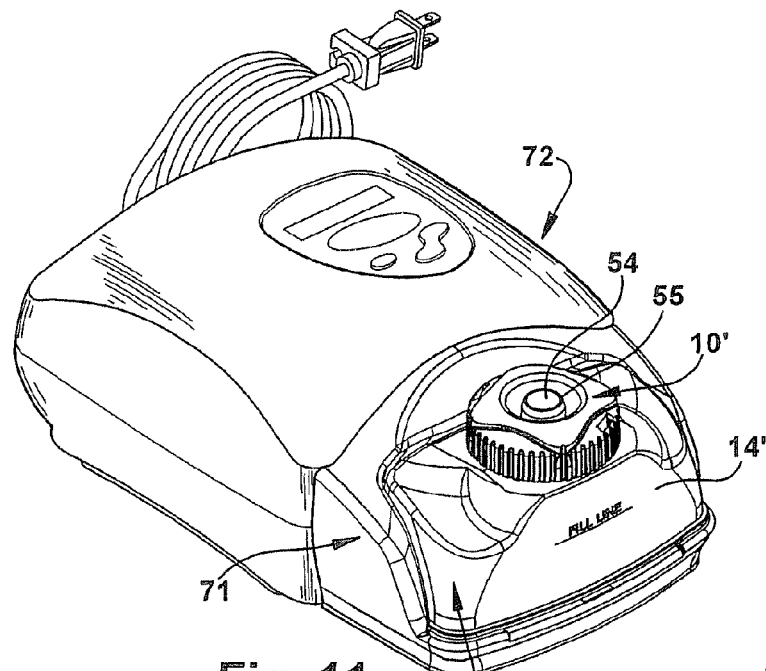
Fig. 11
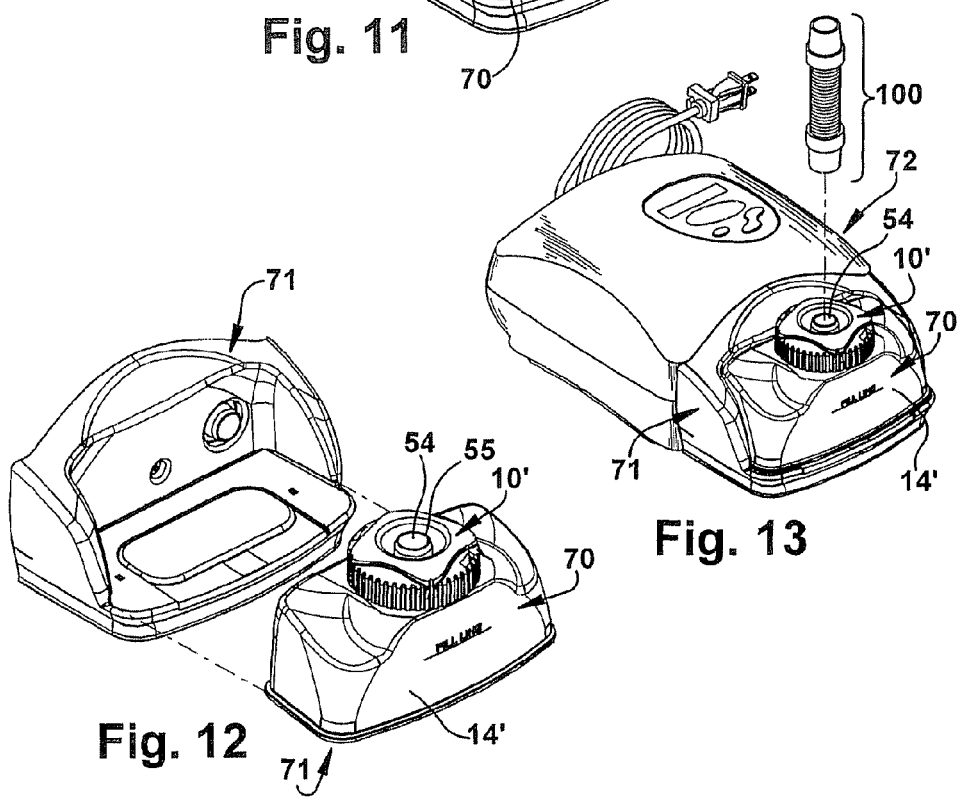
Fig. 12
Fig. 13

US 7,913,985 B2

CAP

RELATED APPLICATIONS

This application claims the benefit of U.S. Provisional Patent Application Ser. No. 60/780,789 filed on Mar. 9, 2006 for RECEPTACLE CAP, the entire disclosure of which is fully incorporated herein by reference.

BACKGROUND

A variety of caps are used to close receptacles. Caps may be secured to receptacles by cooperating threads. A seal may be formed between the cap and the receptacle to inhibit a fluid from leaking out of the assembled cap and receptacle.

Ventilators and other positive pressure airway devices apply breathing gasses to a patient's airways. In some instances, discomfort may arise from dryness of the airways caused by the breathing gas. In such instances, humidification is used to comfort the patient. Humidification adds moisture to the breathing gases to thereby reduce dryness of the airway. Humidifiers of ventilators and other positive pressure airway devices typically include a water reservoir. Water in the reservoir may be heated to add the moisture to the air.

SUMMARY

The present application discloses a container cap for providing a seal with an annular wall of a receptacle. The cap includes a top wall, an annular seal wall, and cam structure. The annular seal wall extends axially from the cover portion. The annular seal wall is spaced radially inward of the cam structure. An end portion of the annular seal wall is configured to form a seal with the annular wall of the receptacle when the end portion is forced into engagement with the annular wall of the receptacle.

BRIEF DESCRIPTION OF THE DRAWINGS

In the accompanying drawings which are incorporated in and constitute a part of the specification, embodiments of the invention are illustrated, which, together with a general description, and the detailed description given below, serve to provide examples of the principles of this invention.

FIG. 11 is a perspective view of one embodiment of a continuous positive airway pressure (CPAP) device that includes a humidifier assembly;

FIG. 12 is an exploded perspective view of one embodiment of a humidifier assembly;

FIG. 13 is a perspective view of one embodiment of a CPAP device showing coupling of a hose to an outlet port of a humidifier assembly;

DESCRIPTION

Figure 1:
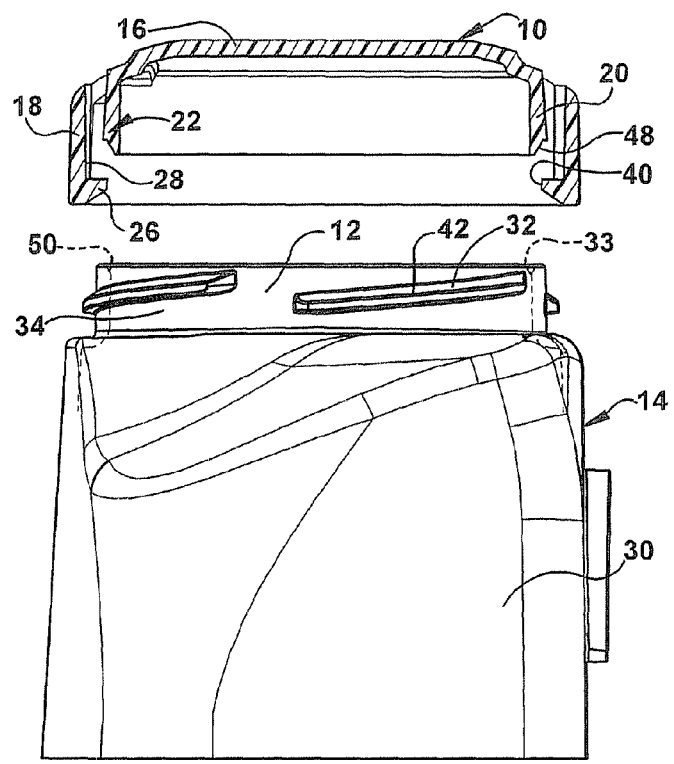
FIG. 1 is an illustration of one embodiment of a cap (shown in section) positioned to be assembled with a receptacle.
Figure 2:
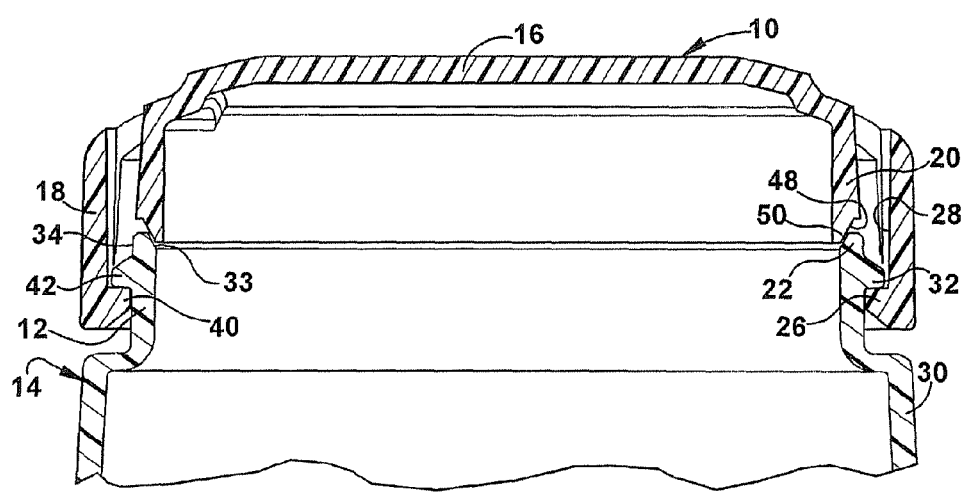
FIG. 2 is a sectional view of one embodiment of a cap being assembled with a receptacle.
Figures 7, 7A:
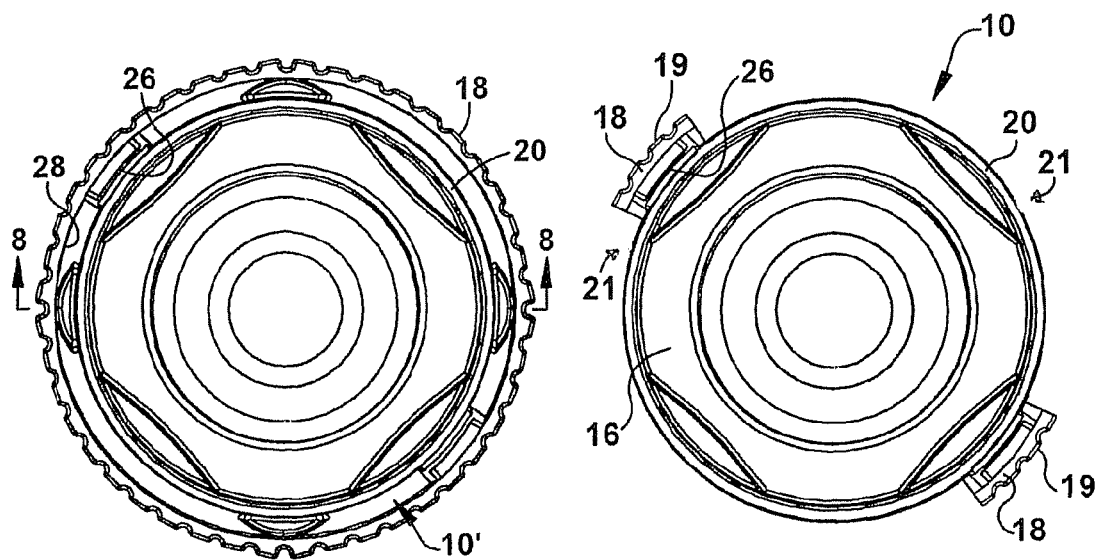
FIG. 7 is a view taken along lines 7-7 in FIG. 6.
Figure 8:
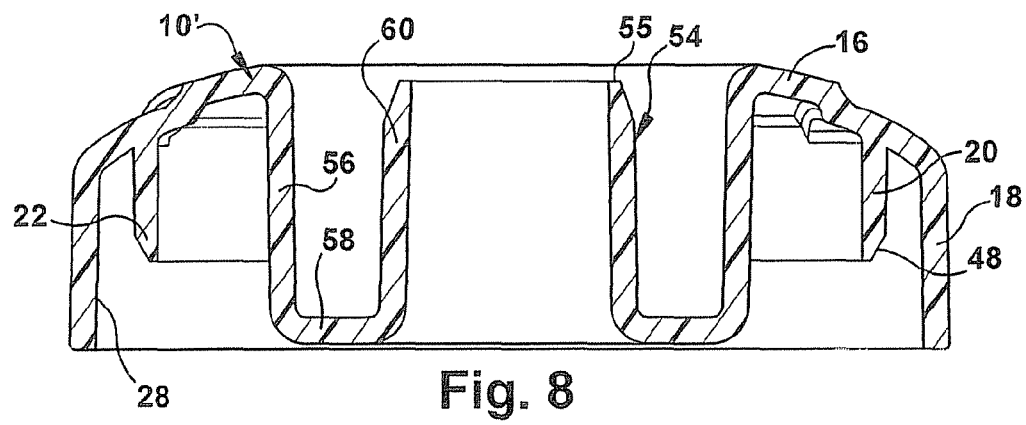
FIG. 8 is a sectional view taken along the plane indicated by lines 8-8 in FIG. 7.
Figure 9:
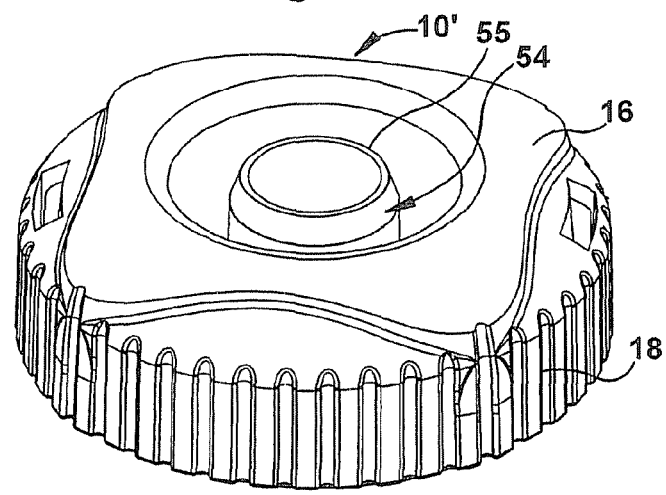
FIG. 9 is a perspective view of one embodiment of a cap that includes a port showing the top of the cap.
Figure 10:
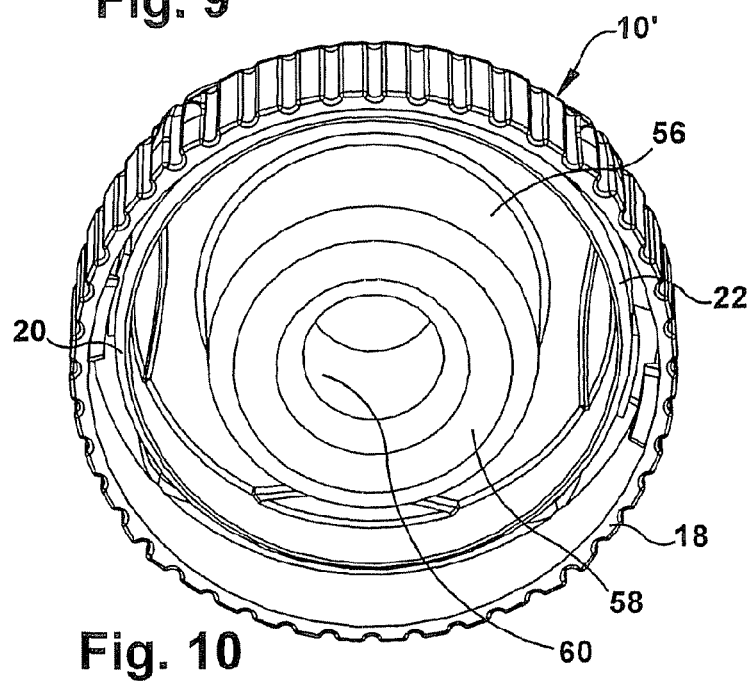
FIG. 10 is a perspective view of one embodiment of a that includes a port showing the underside of the cap.
Figure 14:
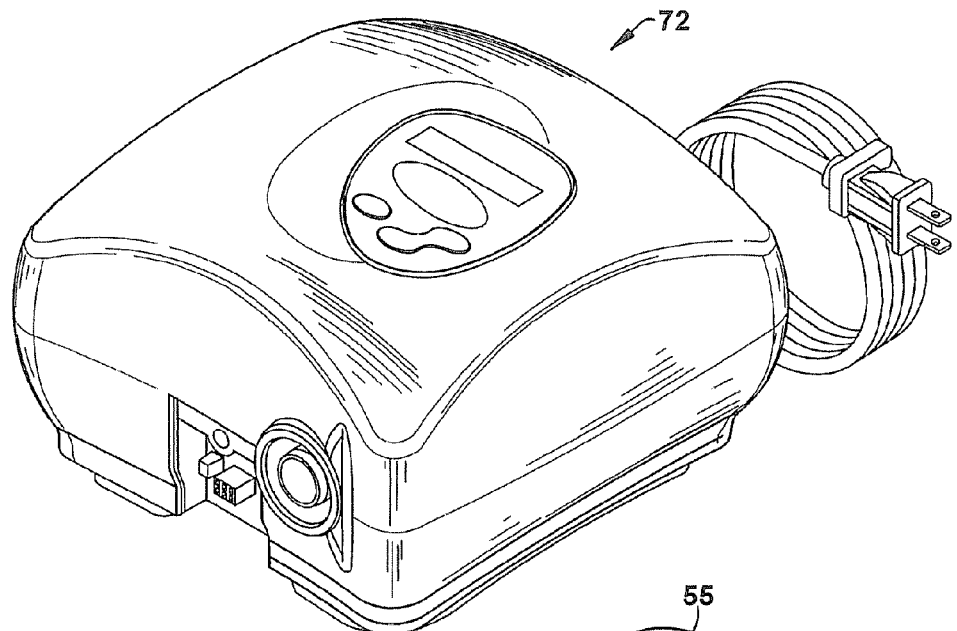
FIG. 14 is a perspective view of one embodiment of a CPAP device.

FIGS. 1 and 2 illustrate one embodiment of a container cap 10 for providing a seal with an annular wall 12 of a receptacle 14. The cap 10 includes a top wall 16, an outer wall 18, and an inner annular wall or annular seal wall 20. The outer wall 18 extends axially from the cover portion 16. The outer wall 18 may be a continuous annular wall (see FIGS. 7 and 10) or the outer wall may include segments 19 with spaces or gaps 21 between the segments (see FIG. 7A). FIG. 7A shows an embodiment where the outer wall includes two small segments 19 and two large gaps 21. However, any configuration of segment sizes, gap sizes and number of segments may be employed.

Referring to FIGS. 1 and 2, the inner annular wall or seal wall 20 also extends axially from the cover portion 16 in generally the same direction as the outer wall and is spaced radially inward of the outer wall. The inner wall 20 is continuous in the illustrated embodiments (see FIGS. 7 and 10). An end portion 22 of the seal wall 20 is configured to form a seal with the annular wall 12 of the receptacle 14 when the end portion 22 is forced into engagement with the annular wall of the receptacle. In the illustrated embodiment, the end portion 22 is tapered to enhance sealing with the annular wall 12 of the receptacle 14. However, the end portion 22 of the inner annular wall 20 may take any configuration that is conducive to sealing with the receptacle wall 12. The seal wall 20 may be configured to flex radially inward to enhance sealing with the annular wall 12 of the receptacle.

In one embodiment, the cap 10 is sized to facilitate cleaning and filling of the receptacle. For example, the cap may be sized to allow insertion of a user's hand or a portion of the user's hand, such as a user's fingers. The diameter of the inner annular wall or seal wall 20 may also be greater than two inches in diameter. For example, the diameter of the seal wall 20 may be between two and six inches.

In the embodiment illustrated by FIGS. 1 and 2, a first cam structure 26 is defined on an inner surface 28 of the outer wall 18. The receptacle 14 includes a compartment portion 30 that defines an interior space of the receptacle, and the annular wall 12 extending axially from the compartment portion. A second cam structure 32 is defined on an outer surface 34 of the annular wall of the receptacle. When the cap 10 is assembled with the receptacle 12 and is rotated, the first and second cam structures 26, 32 engage one another. Engagement between the cam structures 26, 32 moves the annular seal wall 20 of the cap into engagement with the annular wall 12 of the receptacle 14 to form a seal between the cap and the receptacle. In one embodiment, the inner annular wall 20 of the cap 10 engages an inner surface 33 of an annular wall 12 of the reservoir 14 to form the seal. The inner surface 33 may be an inner side of the receptacle wall 12 or a tapered surface 50 formed at the end of the receptacle wall. In one embodiment, the engagement between the wall 12 of the receptacle and the inner annular wall 20 of the cap provides an air and water tight seal without using any secondary material or gasket. In another embodiment, a gasket may also be included.

In the embodiment illustrated by FIGS. 1 and 2, the first cam structure 26 comprises a pair of protrusions 40 that extend radially inward from the outer wall 18. The second cam structure 32 comprises helical thread portions 42 that extend radially outward from an outer surface 44 of the annular wall 12. When the cap is rotated, the protrusions 40 follow the thread portions 42 to axially move the cap. The cam structures 26, 32 can take a wide variety of different forms. For example, threads can be formed on the cap 10 and the receptacle 14, threads can be formed on the cap 10 and a following protrusion is formed on the receptacle wall 12. Any arrangement where rotation of the cap 10 relative to the receptacle 14 causes relative axial movement of the cap 10 with respect to the receptacle 14 can be employed.

In the embodiment illustrated by FIGS. 1 and 2, the annular seal wall 20 includes a taper 48 and the annular wall 12 of the receptacle 14 includes a taper 50. The taper 48 of the annular seal wall engages the taper 50 of the annular wall of the receptacle. The tapers 48, 50 enhance the seal between the cap 10 and the receptacle 14. The tapers 48, 50 can be replaced with any contour that facilitates sealing between inner annular wall 20 and the receptacle annular wall 12. In one embodiment, the inner annular wall 20 is tapered and the annular wall 12 is not tapered. In another embodiment, the inner annular wall 20 is not tapered and the annular wall 12 is tapered. Any arrangement that facilitates sealing between inner annular wall 20 and the wall 12 may be employed.

The cap 10 and the receptacle 14 can be made from a wide variety of different materials. For example, the receptacle 14 and/or the cap 10 can be made from plastic polymers such as ABS, Polystyrene, Polycarbonate, and other plastic materials.

Figure 3:
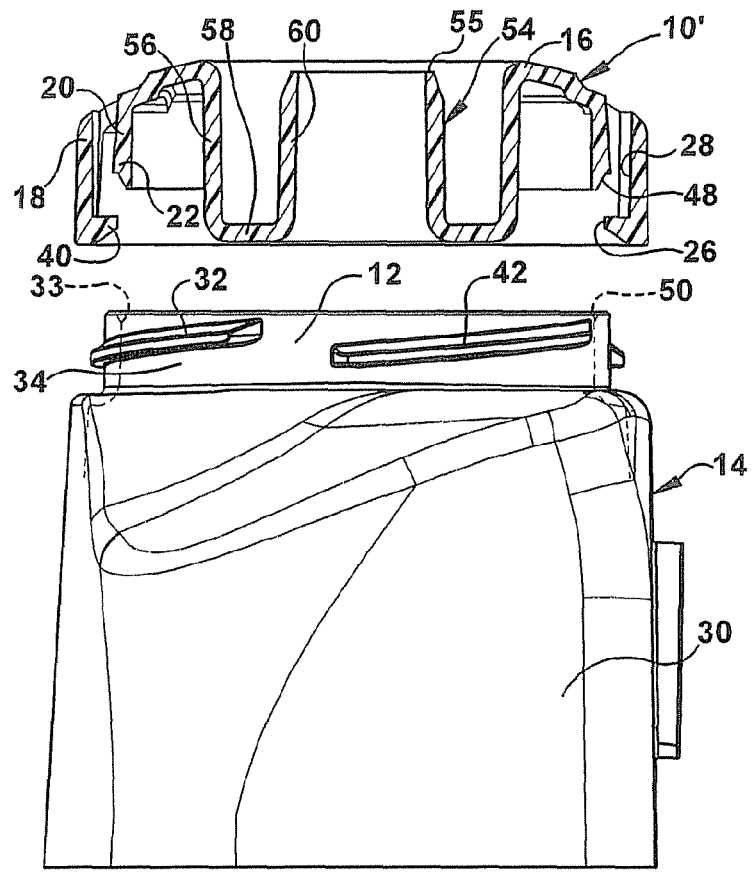
FIG. 3 is an illustration of one embodiment of a cap (shown in section) that includes a port positioned to be assembled with a receptacle.
Figure 4:
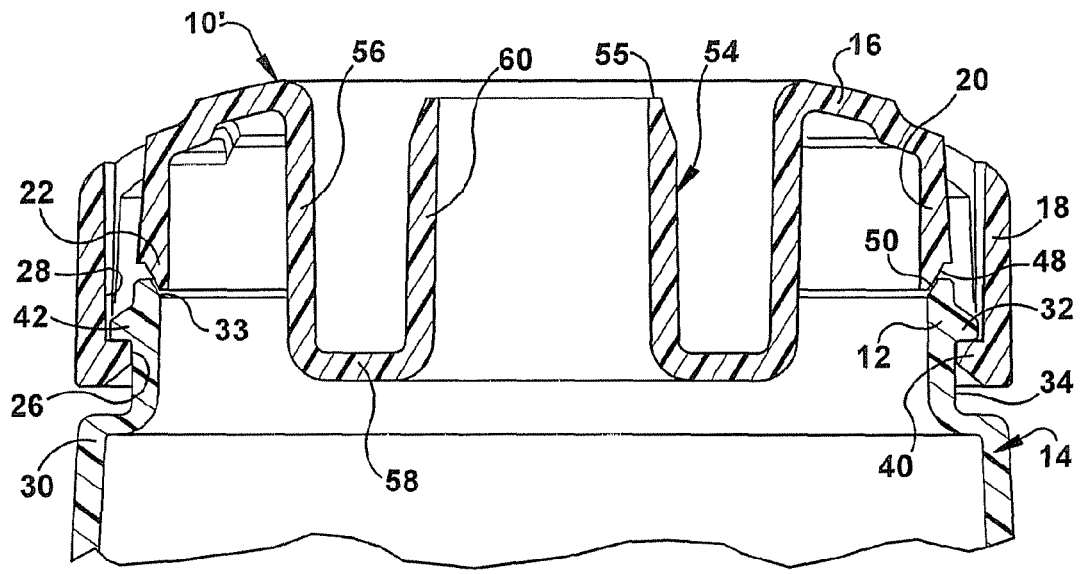
FIG. 4 is a sectional view of one embodiment of a cap that includes a port being assembled with a receptacle.
Figure 5:
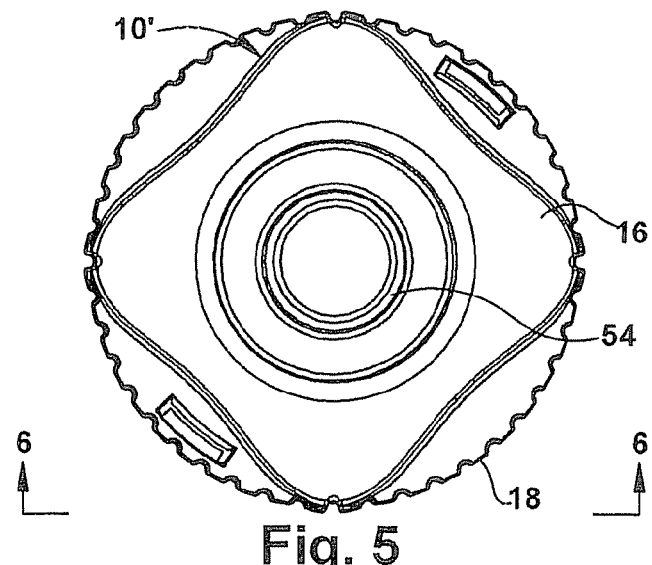
FIG. 5 is a top view of one embodiment of a cap that includes a port.
Figure 6:
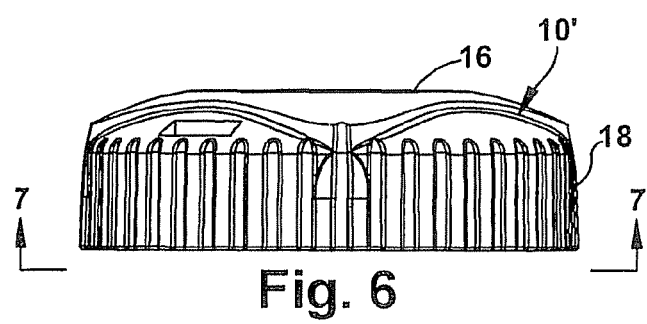
FIG. 6 is a view taken along lines 6-6 in FIG. 5.

FIGS. 3 and 4 illustrate an embodiment where the cap 10' includes a port 54 connected or formed in the top wall 16 for communicating fluid through the cap 10'. The cap 10' illustrated by FIGS. 3 and 4 is substantially the same as the cap 10 illustrated by FIGS. 1 and 2, with the exception of the addition of the port 54. In the exemplary embodiment illustrated by FIGS. 3 and 4, the port 54 has an outlet end 55 that is recessed with respect to the top wall 16 of the cap and is spaced radially inward of the top wall 16. The outlet end 55 may be recessed more than is shown in the illustrated embodiment or the outlet end 55 may be flush with the top wall 16 of the cap 10'. By recessing the port 54 or configuring the port 54 to be flush with the top wall 16, the likelihood of the port 54 being broken off is reduced. In another embodiment, a portion of the port 54 is recessed and a portion of the port extends past the top wall 16. In another embodiment, the entire port 54 extends outward from the top wall 16.

Figure 20:
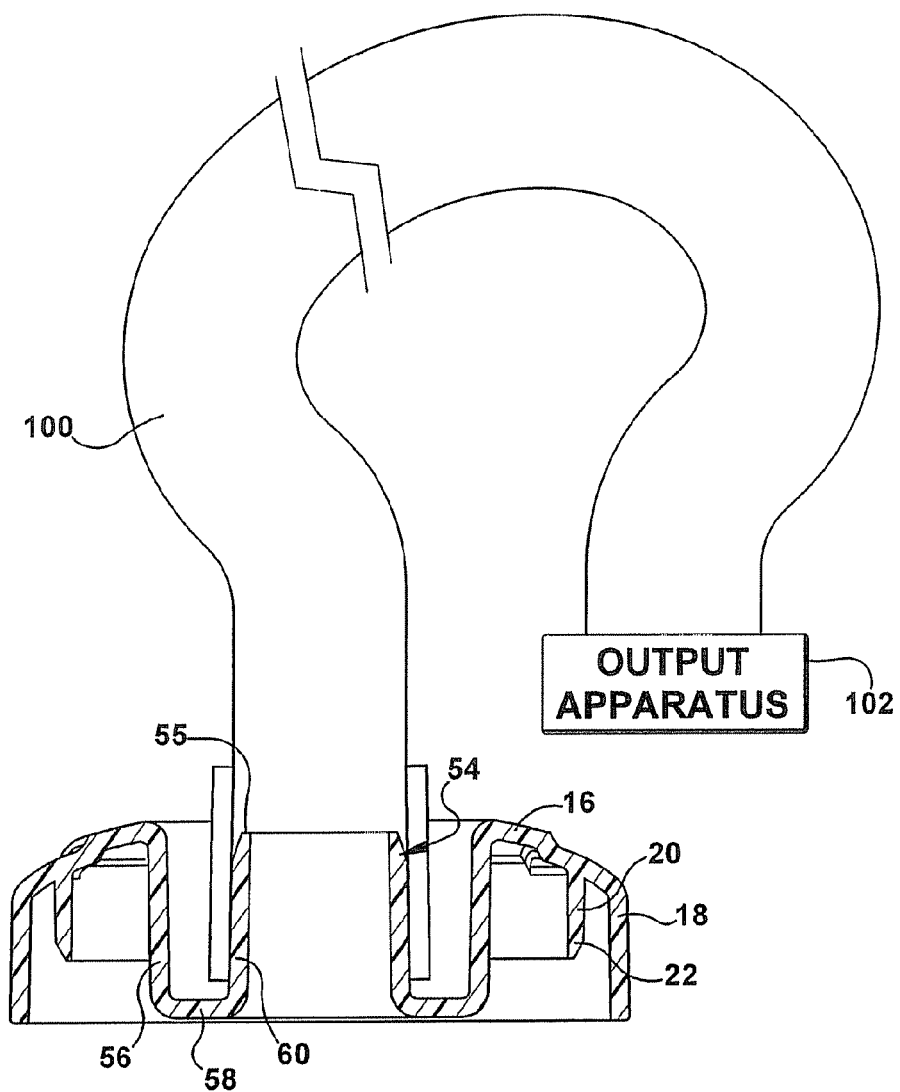
FIG. 20 illustrates one embodiment of a hose assembly coupled to a port of a cap.

The illustrated recessed port 54 is formed by an annular wall 56 that extends axially away from the top wall 16, an inner end wall 58 that extends radially inward from the annular wall 56, and an annular wall 60 that extends axially from the end wall 58 back toward the top wall 16. The illustrated port 54 is but one of a wide variety of different port configurations that may be employed Any port configuration may be used that allows for connection with a tube or hose to communicate fluid through the cap 10'. FIG. 20 illustrates an example of a hose 100 coupled to a port 54 of the cap 10'. The hose communicates fluid from the cap to an output device or apparatus 102 such as, for example, a nasal cannula, a nose mask or a face mask. In one embodiment, the hose provides pressurized air from a CPAP device. In this embodiment, the output device or apparatus 102 is a CPAP mask.

The features of the disclosed caps 10, 10' and receptacle 14 may be implemented in a wide variety of different applications. For example, any one or more of the features of the caps 10, 10' and receptacle 14 may be used to form a container assembly for any application that requires a seal to be formed between the cap and the receptacle. Referring to FIGS. 11-16, an example of one application for features of the disclosed cap 10' and a receptacle 14 is in a humidifier reservoir assembly 70 for a continuous positive airway pressure device 72. The features of the caps 10, 10' and receptacle 14 can be implemented in any humidifier reservoir assembly. For example, the features of the cap 10, 10' and receptacle 14 can be implemented in a humidifier reservoir assembly 70 that is designed to conduct heat from a heat source 71 to fluid in the reservoir assembly 70 or the features of the cap 10, 10' and receptacle 14 can be implemented in a humidifier reservoir assembly that is designed to be heated by induction. The fluid in the humidifier reservoir assembly can be heated in any manner. For example, the humidifier reservoir assembly 70 can be used in the commercially available INVACARE POLARIS EX heated humidifier.

Figure 15:
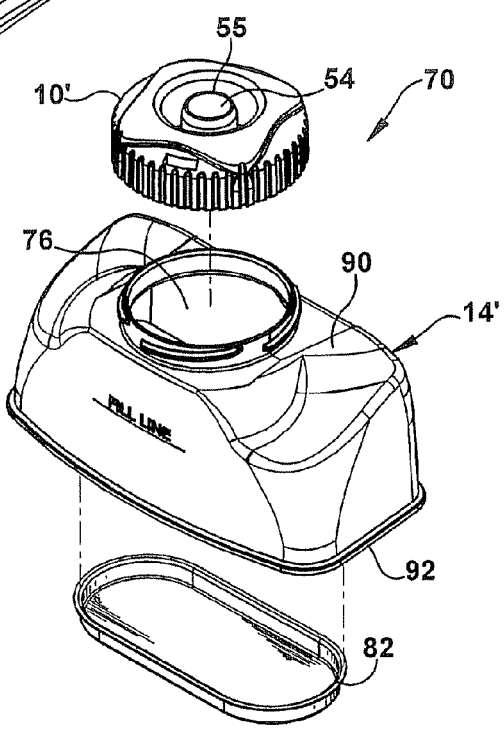
FIG. 15 is an exploded perspective view of one embodiment of a humidifier reservoir assembly.

Referring to FIG. 15, the illustrated humidifier reservoir assembly 70 includes a cap 10', a reservoir body 14', and a heat transfer plate 82. Referring to FIGS. 12 and 15, the fluid in the illustrated humidifier reservoir assembly 70 is heated by a conducting heat through the heat transfer plate 82 (FIG. 15) with the heat source 71 (FIG. 12). U.S. patent application Ser. No. 11/522,682, filed on Sep. 18, 2006, entitled System and Method for Humidifying a Breathing Gas describes a humidifier with an induction water heating mechanism and is incorporated herein by reference in its entirety.

Figure 16:
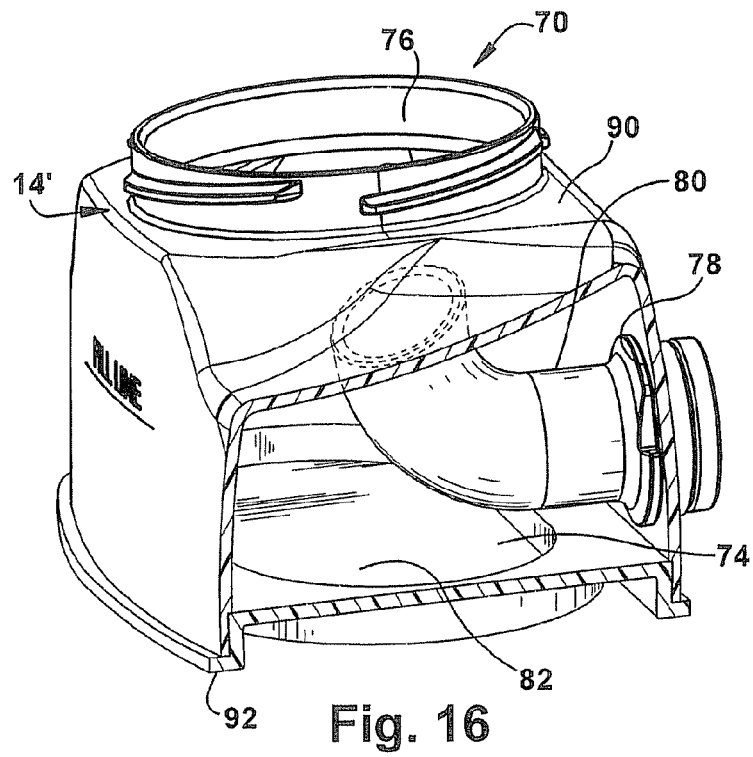
FIG. 16 is a perspective view of one embodiment of the humidifier reservoir assembly of FIG. 15 with a portion cut away to illustrate assembly of an inlet conduit with the reservoir.
Figure 17:
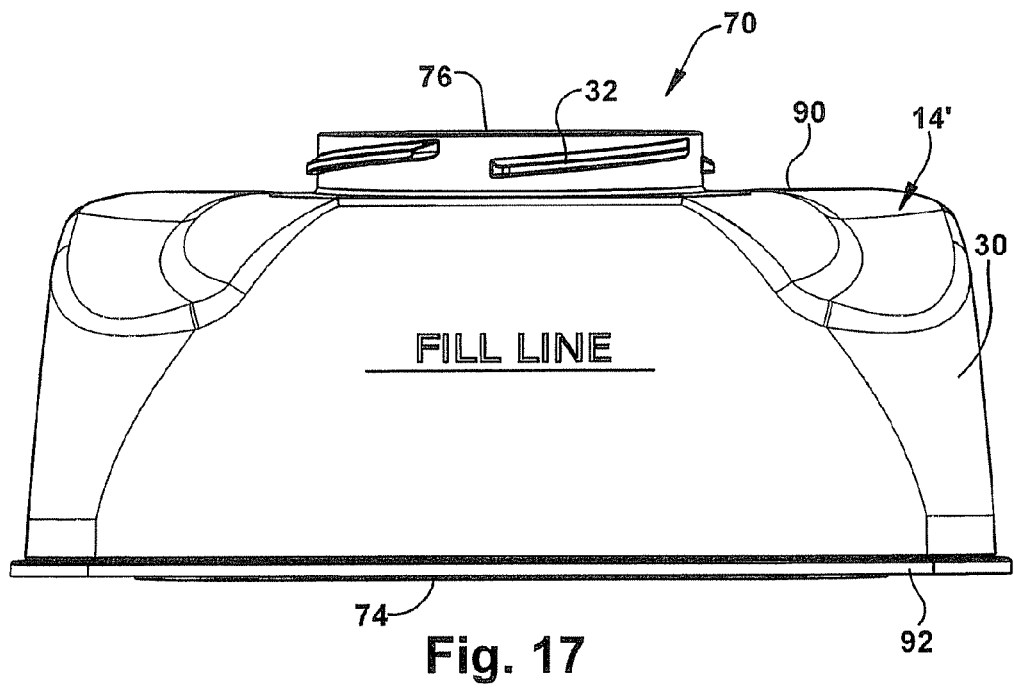
FIG. 17 is a front view of the reservoir of a humidifier assembly of FIGS. 15 and 16.
Figure 18:
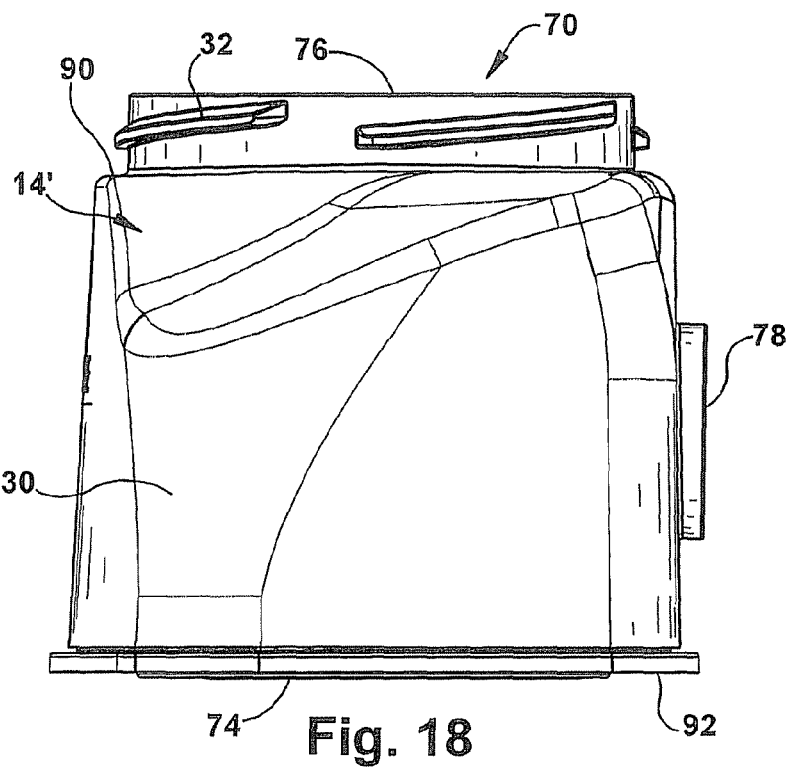
FIG. 18 is a side view of the reservoir of FIGS. 15 and 16.
Figure 19:
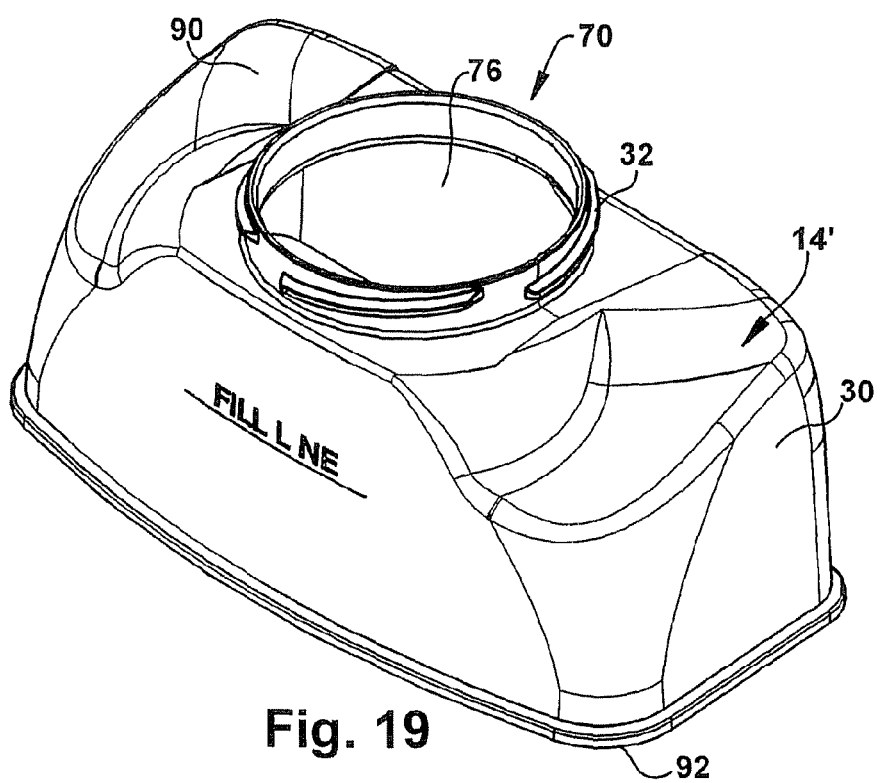
FIG. 19 is a perspective view of the reservoir of FIGS. 15 and 16.

Referring to FIG. 16, the reservoir body 14' includes a plate opening 74, a cap opening 76 and conduit opening 78. The reservoir body 14' is substantially the same as the receptacle 14 described above, except the reservoir body 14' includes the plate opening 74 and the conduit opening 78. The conduit 80 is a disposed in the conduit opening 78 for supplying fluid under pressure to the receptacle reservoir assembly 70. The heat transfer plate 82 is disposed in the plate opening 74 such that a seal is formed between the plate and the reservoir body 14', such that the reservoir assembly can be filled with a fluid such as water. In the exemplary embodiment, the reservoir body 14' is constructed from a plastic material and the plate 82 is made from a metal material, though other materials may also be used. The plate 82 is included in the assembly to transfer heat to a fluid, such as water, disposed in the reservoir assembly 70. The cap seals the cap opening 76. The cap may be the cap 10', which seals with the receptacle as described above or the cap may be a cap that seals with the receptacle in another manner. As previously described, the cap includes an outlet port 54 for communicating fluid under pressure out of the receptacle 14' in the illustrated embodiment. In another embodiment, the outlet port 54 is formed in the receptacle body.

The cap opening 76 for the receptacle body 14' of the humidifier reservoir assembly 70 may be sized to accept an average size human hand or at least a portion of hand, such as two or more fingers. For example, the cap opening 76 may be between two and six inches in diameter. Referring to FIGS. 15 and 16, the cap opening 76 is positioned with respect to the plate opening 74 to allow the plate 82 to be removed by inserting an object, such as a hand or an elongated object like a pen, through the cap opening 76 and pressing on the plate. In the example illustrated by FIGS. 15 and 16, the cap opening 76 is disposed through an upper surface 90 of the receptacle and the plate opening 74 is disposed through a lower surface 92 of the receptacle.

The large size of the cap opening 76 above the fill line facilitates easy disassembly and cleaning of the components of the humidifier reservoir assembly and easy filling of the reservoir. The humidifier reservoir assembly 70 can be cleaned by insertion of the user's hand through the cap opening or insertion of a finger or fingers through the cap opening 76. The user can then press on the heat transfer plate with the his or her hand to remove the heat transfer plate from the receptacle. The receptacle and the heat transfer plate can then be washed.

It should be understood that the embodiments discussed above are representative of aspects of the invention and are provided as examples and not an exhaustive description of implementations of an aspect of the invention.

While various aspects of the invention are described and illustrated herein as embodied in combination in the exemplary embodiments, these various aspects may be realized in many alternative embodiments, either individually or in various combinations and sub-combinations thereof. Unless expressly excluded herein all such combinations and sub-combinations are intended to be within the scope of the present invention. Still further, while various alternative embodiments as to the various aspects and features of the invention, such as alternative materials, structures, configurations, methods, devices, software, hardware, control logic and so on may be described herein, such descriptions are not intended to be a complete or exhaustive list of available alternative embodiments, whether presently known or later developed. Those skilled in the art may readily adopt one or more of the aspects, concepts or features of the invention into additional embodiments within the scope of the present invention even if such embodiments are not expressly disclosed herein. Additionally, even though some features, concepts or aspects of the invention may be described herein as being a preferred arrangement or method, such description is not intended to suggest that such feature is required or necessary unless expressly so stated. Still further, exemplary or representative values and ranges may be included to assist in understanding the present invention, however, such values and ranges are not to be construed in a limiting sense and are intended to be critical values or ranges only if so expressly stated.

The invention claimed is:

1. A humidifier reservoir cap for providing a seal with an annular wall of a humidifier reservoir, the cap comprising:
    a top wall;
    a port defined by an annular wall having an outlet end that is recessed with respect to the top wall and is spaced radially inward of the top wall;
    an annular sealing wall extending axially from the top wall and spaced radially outward of the annular wall of the port, the annular sealing wall including an end portion that is configured to form a seal with the annular wall of the receptacle when the end portion is forced into engagement with the annular wall of the receptacle;
    a cam structure spaced radially outward of the sealing wall, the cam structure being configured to engage the humidifier reservoir and force annular sealing wall into engagement with the annular wall of the reservoir to provide the seal between the cap and the annular wall of the humidifier reservoir.

2. The cap of claim 1 wherein the cap is formed from a single piece of material.

3. The cap of claim 1 wherein the end portion of the annular sealing wall is tapered.

4. The cap of claim 1 wherein the annular sealing wall is greater than two inches in diameter.

5. The cap of claim 1 wherein the annular sealing wall is between two and six inches in diameter.

6. The cap of claim 1 wherein the cam structure is formed on a continuous radially outer wall.

7. A humidifier reservoir cap for providing a seal with an annular wall of a humidifier reservoir, the cap comprising:
    a top wall;
    a port defined by a first annular wall that extends away from the top wall, an inner end wall that extends radially inward from the first annular wall, and a second annular wall that extends axially from the inner end wall back toward the top wall;
    an annular sealing wall extending axially from the top wall and spaced radially outward of the first annular wall of the port, the annular sealing wall including an end portion that is configured to form a seal with the annular wall of the receptacle when the end portion is forced into engagement with the annular wall of the receptacle;
    a cam structure spaced radially outward of the sealing wall, the cam structure being configured to engage the humidifier reservoir and force annular sealing wall into engagement with the annular wall of the reservoir to provide the seal between the cap and the annular wall of the humidifier reservoir.

8. The cap of claim 7 wherein the end portion of the annular sealing wall is tapered.

9. The cap of claim 7 wherein the cap is formed from a single piece of material.

10. The cap of claim 7 wherein the annular sealing wall is greater than two inches in diameter.

11. The cap of claim 7 wherein the annular sealing wall is between two and six inches in diameter.

12. The cap of claim 7 wherein the cam structure is formed on a continuous radially outer wall.

13. A container assembly comprising:
    a cap comprising;
        a top wall;
        a port defined by an annular wall that is recessed with respect to the top wall and is spaced radially inward of the top wall;
        an annular sealing wall extending axially from the top wall and spaced radially outward of the annular wall of the port, the annular sealing wall including an end portion;
        a first cam structure spaced radially outward of the annular sealing wall;
    a receptacle comprising:
        a compartment portion that defines an interior space of the receptacle;
        an annular wall extending axially from the compartment portion;
        a second cam structure defined on an outer surface of the annular wall of the receptacle;
        wherein the first and second cam structures engage one another upon rotation of the cap with respect to the receptacle to move the annular sealing wall of the cap into engagement with the annular wall of the receptacle to form a seal therebetween.

14. The container assembly of claim 13 wherein the annular sealing wall is tapered.

15. The container assembly of claim 13 wherein the annular wall of the receptacle is tapered.

16. The container assembly of claim 13 wherein the annular sealing wall is tapered and the annular wall of the receptacle is tapered and wherein the taper of the annular sealing wall engages the taper of the annular wall of the receptacle.

17. The container assembly of claim 13 wherein the annular sealing wall is greater than two inches in diameter.

18. The container assembly of claim 13 wherein annular sealing wall is between two and six inches in diameter.

19. A humidifier reservoir assembly for a continuous positive airway pressure device comprising:
   a receptacle that includes a plate opening, a cap opening and conduit opening;
   a conduit disposed in the conduit opening for supplying fluid under pressure to the receptacle;
   a plate disposed in the plate opening such that a seal is formed between the plate and the receptacle;
   a cap that seals the cap opening, the cap including an outlet port for communicating fluid under pressure out of the receptacle.

20. The humidifier reservoir assembly of claim 19 wherein the cap comprises:
   a cover portion;
   an outer wall extending axially from the cover portion;
   an inner annular wall extending axially from the cover portion and spaced radially inward of the outer annular wall,
   wherein the inner annular wall engages the receptacle to form a seal with the receptacle.

21. The humidifier reservoir assembly of claim 19 wherein the outlet port is defined by a first annular wall that extends away from a top wall of the cap, an inner end wall that extends radially inward from the first annular wall, and a second annular wall that extends axially from the inner end wall back toward the top wall.

22. The humidifier reservoir assembly of claim 19 wherein the outlet port is defined by an annular wall having an outlet end that is recessed with respect to a top wall of the cap and is spaced radially inward of the top wall.

23. The humidifier reservoir assembly of claim 19 wherein the cap opening is sized to accept an average size human hand.

24. The humidifier reservoir assembly of claim 19 wherein the cap opening is greater than two inches in diameter.

25. The humidifier reservoir assembly of claim 19 wherein the cap opening is between two and six inches in diameter.

26. The humidifier reservoir of claim 19 wherein the cap opening is positioned with respect to the plate opening to allow the plate to be removed by inserting an object through the cap opening and pressing on the plate.

27. The humidifier reservoir of claim 20 wherein the cap opening is disposed through an upper surface of the receptacle and the plate opening is disposed on a lower surface of the receptacle.

28. A humidifier reservoir assembly for a continuous positive airway pressure device comprising:
   a receptacle that includes a plate opening, a cap opening and conduit opening;
   a conduit disposed in the conduit opening for supplying fluid under pressure to the receptacle;
   a plate disposed in the plate opening such that a seal is formed between the plate and the receptacle;
   a cap that seals the cap opening, wherein the cap opening is sized to accept a human hand of average size.

29. The humidifier reservoir assembly of claim 28 wherein the cap comprises:
   a cover portion;
   an outer annular wall extending axially from the cover portion;
   an inner annular wall extending axially from the cover portion and spaced radially inward of the outer annular wall,
   wherein the inner annular wall engages the receptacle to form a seal with the receptacle.

30. The humidifier reservoir assembly of claim 28 wherein the cap opening is greater than two inches in diameter.

31. The humidifier reservoir assembly of claim 28 wherein the cap opening is between two and six inches in diameter.

32. The humidifier reservoir of claim 28 wherein the cap opening is positioned with respect to the plate opening to allow the plate to be removed by inserting an object through the cap opening and pressing on the plate.

33. The humidifier reservoir of claim 28 wherein the cap opening is disposed through an upper surface of the receptacle and the plate opening is disposed on a lower surface of the receptacle.

* * * * *